United States Patent [19]

Broger et al.

[11] Patent Number: 5,514,805
[45] Date of Patent: May 7, 1996

[54] ASSYMETRIC SYNTHESIS PROCESS

[75] Inventors: Emil A. Broger, Magden; Werner Hofheinz, Bottmingen; Arthur Meili, Riehen, all of Switzerland

[73] Assignee: Hoffmann-La Roche Inc., Nutley, N.J.

[21] Appl. No.: 225,408

[22] Filed: Apr. 8, 1994

Related U.S. Application Data

[63] Continuation of Ser. No. 10,120, Jan. 28, 1993, abandoned.

[30] Foreign Application Priority Data

Jan. 31, 1992 [CH] Switzerland ............... 289/92

[51] Int. Cl.$^6$ ............................... C07D 401/06
[52] U.S. Cl. ............... 546/176; 546/255; 546/178
[58] Field of Search ............. 546/178, 176, 546/255

[56] References Cited

U.S. PATENT DOCUMENTS 4,861,890  8/1989  Heiser et al. ............... 546/184

FOREIGN PATENT DOCUMENTS 0026894  9/1980  European Pat. Off. .

OTHER PUBLICATIONS

Noyori, et al., J. Am. Chem. Soc. 110, 629–631 (1988).
Hayashi, et al., Tetrahedron Letters, 425–428 (1979).
Marko, et al., J. Organometallic Chem. 232, C17–C19 (1982).
Achiwa, et al., Tetrahedron Letters, 363–366 (1989).
Sakuraba., Chemical Abstracts, vol. 116, (1992).
Arntz, et al., Catal. Met. Complexes 161–189 (1991).

Primary Examiner—David B. Springer
Attorney, Agent, or Firm—George M. Gould; William H. Epstein; Bruce A. Pokras

[57] ABSTRACT

A novel process for the asymmetric hydrogenation of compounds of the formula:

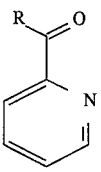

II wherein R represent aryl or heteroaryl,
to compounds of the formula:

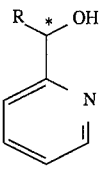

I wherein R has the above significance, is carried out using rhodium-diphosphine complexes.

44 Claims, No Drawings

ASSYMETRIC SYNTHESIS PROCESS

This is a continuation of application Ser. No. 08/010,120 filed Jan. 28, 1993, now abandoned.

The present invention is concerned with a novel process for the manufacture of (R) and, respectively, (S) compounds of the formula:

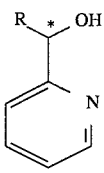

I wherein R represents aryl or heteroaryl.

This process comprises the catalytic, asymmetric hydrogenation a ketone of the formula:

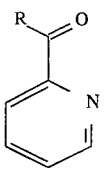

II wherein R has the above significance.

As catalysts there come into consideration rhodium-diphosphine complexes of the formula:

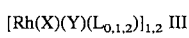

III wherein X, Y and L are:

X=halogenide, Z—COO⁻, phenolate or halogenated phenolate;

Z=lower alkyl, phenyl, halogenated lower alkyl or halogenated phenyl;

Y=chiral, atropisomeric diphosphine ligand of the formula:

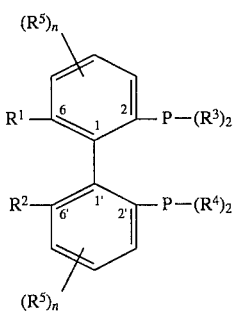

IV or of the formula:

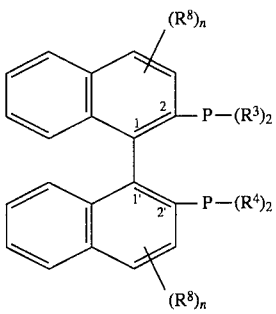

V or a ferrocenyl-diphosphine of the formula:

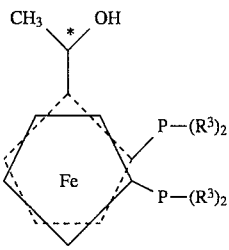

VI wherein:

$R^1$ and $R^2$ independently=lower alkyl, lower alkoxy, di-lower alkylamino, hydroxy, protected hydroxy, hydroxymethyl, protected hydroxymethyl, or $R^1$ and $R^2$ together are the groups:

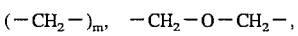

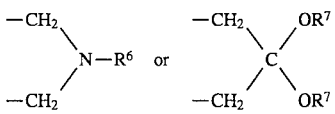

wherein:
m=integer 3, 4, or 5,
$R^6$=lower alkyl, phenyl, or benzyl,
$R^7$=lower alkyl or both $R^7$'s together are di- or trimethylene,
$R^3$ and $R^4$ independently of each other=lower alkyl, phenyl, cycloalkyl, a five-membered heteroaromatic group or a group of the formula:

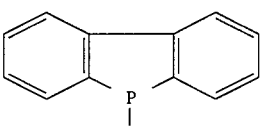

$R^5$=lower alkyl or lower alkoxy,
$R^8$=methyl, ethyl, halogen —OH, —NH₂, acetylamino, —NO₂, or —SO₃H, preferably in the 5,5'-position,
n=integer 0, 1, 2, or 3 and
L=neutral ligand.

The term "lower alkyl" signifies in the scope of the present invention straight-chain or branched alkyl groups with 1 to 4 carbon atoms such as methyl, ethyl, propyl, isopropyl, n-butyl, isobutyl and tert.butyl. The term "lower alkoxy" signifies groups in which the alkyl residue has the foregoing significance. As protecting groups for the hydroxy group or the hydroxymethyl group, there come into consideration in the scope of the present invention especially the usual ether-forming groups such as, e.g., benzyl, allyl, benzyloxymethyl, lower alkoxymethyl or also 2-methoxyethoxymethyl and the like. The term "five-membered heteroaromatic group" stands in the scope of the present invention for one of the substituents of the formulae:

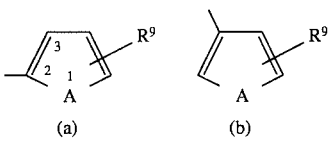

(a)     (b)

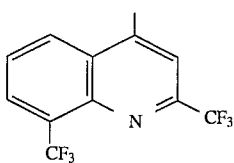

(c)　　　　(d)

In the substituents of formulae (a) to (d), A is oxygen, sulphur or —$NR^{10}$. The substituent $R^9$ is hydrogen, lower alkyl, especially methyl, or lower alkoxy, especially methoxy, and $R^{10}$ is lower alkyl, preferably methyl.

In the scope of the present invention the aforementioned phenyl and benzyl residues can be not only unsubstituted but also substituted in the ortho-, meta- or para-position or also multiply substituted. As substituents there come into consideration phenyl, lower alkyl or lower alkoxy groups, preferably methyl or methoxy groups, or also di-lower alkylamino, preferably dimethylamino groups as well as fluorine or also tri-lower alkylsilyl such as trimethylsilyl and the like.

The term "cycloalkyl" signifies three- to seven-membered rings such as cyclopropyl, cyclobutyl, cyclopentyl, cyclohexyl and cycloheptyl, especially cyclopentyl and cyclohexyl.

The term "halogen" signifies fluorine, chlorine, bromine and iodine.

The terms "aryl" and, respectively, "heteroaryl" signify in the scope of the present invention especially aromatic and, respectively, heteroaromatic hydrocarbons with 4 or 5 to 10 carbon atoms such as especially phenyl, naphthyl, pyridyl, quinolyl and the like. These rings can be not only unsubstituted but also mono- or mutiply-substituted with, e.g., lower alkyl, —$CF_3$, halogen, preferably chlorine, or also phenyl which, in turn, can be unsubstituted or substituted with —$CF_3$ and/or chlorine.

Preferred residues for R are pyridyl and quinolyl, especially 4-pyridyl and 4-quinolyl, which are unsubstituted or preferably substituted with —$CF_3$ and/or chlorine.

An especially preferred residue R is a group of the formula:

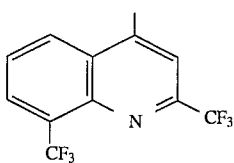

The term "neutral ligand" signifies in the scope of the present invention a readily exchangeable ligand such as olefins, e.g., ethylene, propylene, cyclooctene, 1,5-hexadiene, norbornadiene, 1,5-cyclooctadiene and the like, nitriles such as acetonitrile and benzonitrile, or also the solvent which is used, etc. This ligand can be exchanged during the hydrogenation. Where more than one such ligand is present, these can also be different from one another.

The asymmetric hydrogenations can be carried out in suitable organic solvents which are inert under the reaction conditions. As such there can especially be named aromatic hydrocarbons such as benzene or toluene, cyclic ethers such as tetrahydrofuran or dioxan, esters such as, e.g., ethyl acetate, or also mixtures thereof and the like. The ratio between rhodium and the ligand Y conveniently lies between about 0.05 and about 5 mol, preferably between about 0.5 and about 2 mol, of rhodium per mol of ligand. The ratio between rhodium and the residue X conveniently lies between about 0.01 and about 20, preferably between about 0.5 and about 10 mol of rhodium per mol of residue X. The molar ratio between rhodium in the complexes of formula III and the compounds of formula II to be hydrogenated conveniently lies between about 0.001 and about 5 mol. %, preferably between about 0.005 and about 0.2 mol. %.

The asymmetric hydrogenations using the complexes of formula III can preferably be carried out at temperatures of about 20° C. to about 140° C., especially of about 60° C. to about 120° C. These hydrogenations are also conveniently carried out under pressure, especially under a pressure of about 1 to 100 bar, preferably 2 to 60 bar.

The ligands of formulae IV, V and VI are known compounds or analogues of known compounds which can be prepared readily in a manner analogous to the preparation of known ligands.

Those compounds of formulae IV and V in which $R^3$ and $R^4$ are identical can be obtained, for example, analogously to the methods described in EP 104375 or also EP 398132.

Those compounds in which $R^3$ and $R^4$ are different from each other can be obtained analogously thereto, but in two steps, e.g., in accordance with the following Formula Scheme:

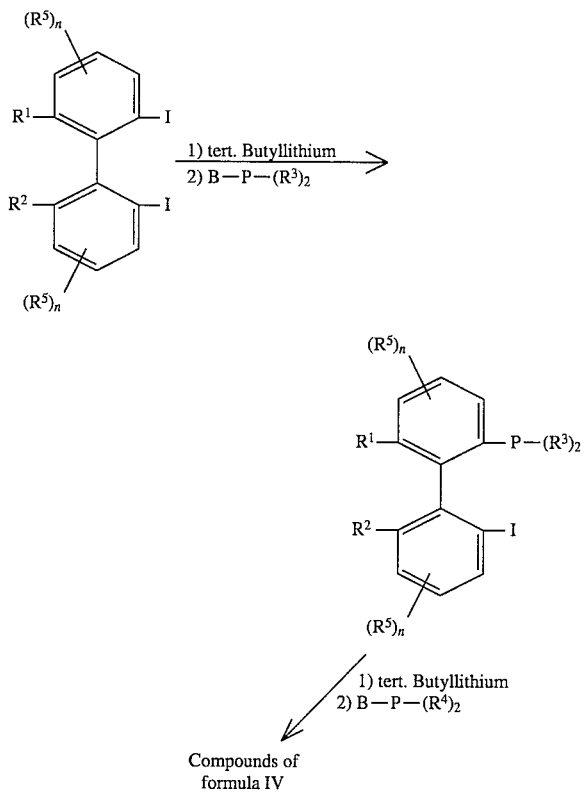

Compounds of formula IV $R^1$, $R^2$, $R^3$, $R^4$, $R^5$, n are as described above, B=leaving group such as, e.g., halogen, especially chlorine or bromine, as well as alkoxy groups such as methoxy and the like.

In order to guarantee that only one iodine is replaced by lithium, the corresponding reactions are conveniently carried out using about equimolar amounts of reaction partners.

The complexes of formula III can be prepared in a manner known per se, e.g., by reacting a compound of formula IV, V or VI with a compound which can yield rhodium, in a suitable, inert organic or aqueous solvent. As suitable compounds which yield rhodium there can be mentioned, for example, organic rhodium complexes with ethylene, propylene and the like, as well as with bis-olefins, e.g. (Z,Z)-1,5-cyclooctadiene, 1,5-hexadiene, bicyclo[2.2.1]hepta-2,5-diene, or with other dienes which form readily soluble complexes with rhodium. Preferred compounds which yield rhodium are, e.g., di-μ-chloro-bis[η⁴-(Z,Z)-1,5-cyclooctadiene]dirhodium(I), di-μ-chloro-bis[η⁴-norbornadiene]dirhodium(I), di-μ-trifluoroacetato-bis[η⁴-(Z,Z)-1,5-cyclooctadiene]dirhodium(I), bis[η⁴-(Z,Z)-1,5-cyclooctadiene]rhodium-tetrafluoroborate or bis[η⁴-(Z,Z)-cyclooctadiene]rhodium-perchlorate.

Of the ligands Y used in the scope of the present invention there are preferred those of formula IV and VI, especially those of formula IV.

Of the ligands of formula IV used in the present invention, n is preferably zero, and $R^1$ and $R^2$ are preferably the same with methyl, methoxy and hydroxy being preferred, especially methyl and methoxy. The preferred groups for $R^3$ and $R^4$ (in no particular order) are: both phenyl, both 3,4,5-trimethoxyphenyl, both cyclohexyl, cyclopentyl and phenyl, isopropyl and phenyl, thienyl and phenyl, cyclohexyl and phenyl, and cyclohexyl and p-tolyl. It is especially preferred that $R^3$ and $R^4$ are different and are phenyl and cyclohexyl.

Of the ligands of formula VI used in the present invention, $R^3$ is preferably phenyl.

The ligand X is preferably a halogenide, Z—COO⁻ (where Z is as described above) or a halogenated phenylate, with the halogenides being especially preferred. Of the halogenides, chloride, bromide and iodide are preferred, with chloride and bromide being especially preferred. Of the group Z—COO⁻, Z is preferably lower alkyl, espcially methyl. Of the halogenated phenylates, a group of the formula $C_6F_5O$ is preferred.

Thus, for the catalyst of formula III it is preferred that X is chlorine or bromine, preferably bromine, and Y is a chiral, atropisomeric ligand of formula IV in which $R^1$ and $R^2$ are identical and are methyl or methoxy, n is 0, and $R^3$ and $R^4$ are different from each other and are phenyl and cyclohexyl.

A preferred embodiment of the process in accordance with the invention is concerned with the manufacture of the (R) and, respectively, (S) enantiomers of the compound of the formula

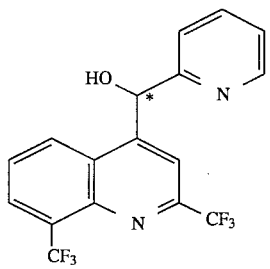

VII by the asymmetric hydrogenation of the compound of the formula

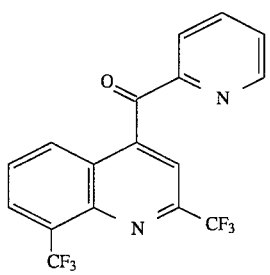

VIII using a catalyst of the invention as described above.

The compound of formula VIII as well as the (R) and (S) compounds of formula VII are known compounds. The latter are intermediates for the manufacture of the enantiomerically pure erythro- and, respectively, threo-isomers of the formula

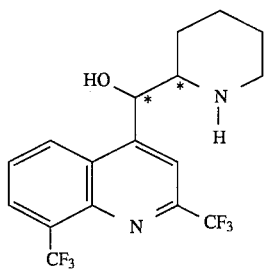

IX

The hydrogenation of the pyridine ring which comes into consideration here can be carried out in a manner known per se, e.g., in the presence of a Pt catalyst, whereby surprisingly no racemization takes place at the C atom carrying the hydroxy group.

The racemic erythro form of the compound of formula IX is a known antimalarial agent under the designation mefloquine.

The process in accordance with the invention permits for the first time an economical access to the optically pure isomers of compounds of formula I, especially mefloquine.

The following Examples illustrate the invention and in no manner represent a limitation thereof. In these Examples the abbreviations used have the following significance:

| | |
|---|---|
| TLC | thin-layer chromatography |
| GC | capillary gas chromatography |
| e.e. | enantiomeric excess. The e.e. of the hydrogenation products was determined by GC on a permethylated cyclodextrin phase. |
| BPPFOH | (1R)-1,1'-bis(diphenylphosphino)-2-[(S)-1-hydroxyethyl]ferrocene |
| BIPHEMP | (6,6'-dimethylbiphenyl-2,2'-diyl)bis-(diphenylphosphine) |
| Cy₂BIPHEMP | P,P-dicyclohexyl-P',P'-diphenyl-(6,6'-dimethylbiphenyl-2,2'-diyl)diphosphine |
| Cy₄BIPHEMP | (6,6'-dimethylbiphenyl-2,2'-diyl)bis-(dicyclohexylphosphine) |
| 2-Thienyl₂BIPHEMP | P,P-diphenyl-P',P'-di-2-thienyl-(6,6'-dimethylbiphenyl-2,2'-diyl)diphosphine |
| HOBIPHEP | (6,6'-dihydroxybiphenyl-2,2'-diyl)bis-(diphenylphosphine) |
| MeOBIPHEP | (6,6'-dimethoxybiphenyl-2,2'-diyl)bis(diphenylphosphine) |
| (3,4,5-TriMeO)-MeOBIPHEP | (6,6'-dimethoxybiphenyl-2,2'-diyl)bis(di-3,4,5-trimethoxyphenyl)phosphine) |
| Cy₂pTolBIPHEMP | P,P-dicyclohexyl-P',P'-di-p-tolyl-(6,6'-dimethylbiphenyl-2,2'-diyl)diphosphine |
| Cy₂MeOBIPHEP | P,P-dicyclohexyl-P',P'-diphenyl-(6,6'-dimethoxybiphenyl-2,2'-diyl)diphosphine |
| Cyp₂MeOBIPHEP | P,P-dicyclopentyl-P',P'-diphenyl-(6,6'-dimethoxybiphenyl-2,2'-diyl)diphosphine |
| Ipr₂MeOBIPHEG | P,P-diisopropyl-P',P'-diphenyl-(6,6'-dimethoxybiphenyl-2,2'-diyl)diphosphine |

The temperatures are given in degrees Celsius.

EXAMPLE 1 a) 6.2 mg (0.0125 mmol) of di-μ-chloro-bis-(1,5-cyclooctadiene)dirhodium(I) and 15.0 mg (0.025 mmol) of (R,S)(−)-BPPFOH were suspended in 20 ml of ethyl acetate in a 50 ml glass flask in a glove box (O₂ content<1 ppm). The suspension was subsequently stirred for 5 minutes, whereby a pale orange, clear solution formed.

b) A 500 ml autoclave was loaded in a glove box (O₂ content<1 ppm) with 1.85 g (5.0mmol) of 2-pyridyl-2,8-bis(trifluoromethyl)-4-quinolyl-ketone, with the catalyst solution prepared above and with 130 ml of ethyl acetate. The hydrogenation was carried out at 60°, a constant pressure of 60 bar of pure $H_2$ and while stirring intensively. After a hydrogenation time of 19 hours the conversion was 84.2% according to GC. The yellow hydrogenation solution was evaporated at 45°/20 mbar on a rotary evaporator. The residue (1.86 g) was dissolved in 5 ml of $CH_2Cl_2$ and filtered through a silica gel column (diameter 2 cm, length 2 cm) in order to separate the catalyst. The product was eluted with 100 ml of $CH_2Cl_2$. The pale yellow filtrate was evaporated at 30°/500 mbar on a rotary evaporator. There were obtained 1.68 g (90.3%) of yellow crystals which contained 84% of (S)-α-(2-pyridyl)-2,8-bis(trifluoromethyl)-4-quinolinemethanol of 82.4% e.e.

EXAMPLE 2 a) 10.2 mg (0.025 mmol) of bis-(1,5-cyclooctadiene)rhodium(I)-tetrafluoroborate, 14.1 mg (0.025 mmol) of (R)-$Cy_2$BIPHEMP and 8.1 mg (0.025 mmol) of tetrabutylammonium bromide were suspended in 20 ml of toluene in a 50 ml glass flask in a glove box ($O_2$ content <1 ppm). The suspension was subsequently stirred for 60 minutes, whereby an orange clear solution formed.

b) A 500 ml autoclave was charged in a glove box ($O_2$ content <1 ppm) with 14.8 g (40 mmol) of 2-pyridyl-2,8-bis(trifluoromethyl)-4-quinolyl-ketone, the catalyst solution prepared above and with 134 ml of toluene. The hydrogenation was carried out at 60°, a constant pressure of 60 bar of $H_2$ and while stirring intensively. After a hydrogenation time of 19 hours the conversion was 100% (TLC). A sample (0.6 g) worked-up analogously to Example 1b) had an e.e. value of 90.4%. The hydrogenation solution remaining was evaporated at 45°/20 mbar on a rotary evaporator. For the crystallization of the product, the residue (13.8 g) was dissolved in 21 ml of hot toluene, cooled slowly to room temperature and stirred for 16 hours. The crystallization was completed by cooling to 1° and stirring for 3 hours. The yellow crystals were filtered off, washed with cold toluene and dried at 50°/20 mbar for 18 hours. There were obtained 12.7 g (92%) of (R)-α-(2-pyridyl)-2,8-bis(trifluoromethyl)-4-quinolinemethanol; m.p.: 130°–131°; TLC 1 spot; 91.8% e.e.; $[\alpha]_D^{20}$+17.1° (c=1, MeOH).

Two-fold recrystallization from ethanol/water yielded pure (R)-enantiomer [(S)-isomer not detectable in the GC]; $[\alpha]_D^{20}$+18.7° (c=1, MeOH); m.p. 136.5°–137.7°.

In an analogous manner there was manufactured:

(S)-α-(2-Pyridyl)-2,8-bis(trifluoromethyl)-4-quinolinemethanol; m.p. 136°–137°; $[\alpha]_D^{20}$–17.8° (c=1 MeOH).

EXAMPLE 3 a) 30.5 mg (0.25 mmol) of benzoic acid and 64.9 mg (0.25 mmol) of tetrabutylammonium hydroxide were dissolved in toluene in a 20 ml graduated flask in a glove box ($O_2$ content 1 ppm) and the solution was adjusted to a volume of exactly 20.0 ml. The clear, colourless solution was stirred for 5 minutes. 10.2 mg (0.025 mmol) of bis-(1,5-cyclooctadiene)rhodium(I)-tetrafluoroborate, 14.1 mg (0.025 mmol) of (R)-$Cy_2$BIPHEMP and 2 ml (0.025 mmol) of the tetrabutylammonium benzoate solution prepared above were added to 20 ml of toluene in a 50 ml glass flask. The suspension was subsequently stirred for 5 minutes, whereby an orange, clear solution formed.

b) A 500 ml autoclave was charged in a glove box ($O_2$ content <1 ppm) with 14.8 g (40 mmol) of 2-pyridyl-2,8-bis(trifluoromethyl)-4-quinolyl-ketone, with the catalyst solution prepared above and with 132 ml of toluene. The hydrogenation was carried out at 60°, a constant pressure of 60 bar of $H_2$ and while stirring intensively. After a hydrogenation time of 19 hours the conversion was 84.3% according to GC. The orange hydrogenation solution was evaporated at 45°/20 mbar on a rotary evaporator. 14.6 g (98%) of brown crystals which contained 84% of (R)-α-(2-pyridyl)-2,8-bis(trifluoromethyl)-4-quinolinemethanol were obtained. A sample (0.6 g) worked-up analogously to Example 1b) had an e.e. of 81.9%.

EXAMPLES 4–22

Hydrogenations set forth in Table I were carried out in a manner analogous to Examples 1–3 using a complex of the formula

[Rh(X)(Y)]

S/C=molar substrate-catalyst ratio
LM=solvent
c=substrate concentration in the hydrogenation mixture
$C_6F_5O$=pentafluoro-phenolate

TABLE 1

Asymmetric hydrogenation of 2-pyridyl 2,8-bis(trifluoromethyl)-4-quinolyl ketone

| Example | X | Y (R) or (S) | S/C | LM | c % | P bar | T °C. | Conversion % | e.e. % |
|---|---|---|---|---|---|---|---|---|---|
| 4 | Cl | BPPFOH | 200 | THF | 1.4 | 60 | 60 | 74.7 | 77.1 |
| 5 | Br | BPPFOH | 200 | Toluene | 1.4 | 60 | 60 | 80.4 | 86.9 |
| 6 | I | BPPFOH | 200 | Toluene | 1.4 | 60 | 60 | 76.9 | 85.2 |
| 7 | Cl | MeOBIPHEP | 200 | Toluene | 1.4 | 60 | 60 | 83.7 | 71.5 |
| 8 | Cl | $Cy_4$BIPHEMP | 200 | Toluene | 1.4 | 60 | 60 | 98.5 | 78.1 |
| 9 | Cl | 2-Thienyl$_2$BIPHEMP | 200 | Toluene | 1.4 | 60 | 60 | 76.3 | 81.3 |
| 10 | Cl | HOBIPHEP | 200 | Toluene | 1.4 | 60 | 60 | 79.5 | 77.2 |
| 11 | Cl | $Cy_2$BIPHEMP | 200 | Toluene | 5.0 | 60 | 60 | 98.5 | 95.2 |
| 12 | Br | $Cy_2$pTolBIPHEMP | 1600 | Toluene | 10.0 | 60 | 60 | 98.4 | 87.5 |
| 13 | Br | $Cy_2$BIPHEMP | 6400 | Toluene | 10.0 | 60 | 60 | 97.4 | 91.3 |
| 14 | Br | $Cy_2$BIPHEMP | 6400 | Toluene | 10.0 | 60 | 100 | 98.9 | 79.0 |
| 15 | Br | $Cy_2$BIPHEMP | 6400 | Toluene | 10.0 | 15 | 80 | 90.2 | 86.2 |
| 16 | Br | $Cy_2$BIPHEMP | 6400 | Toluene | 20.0 | 60 | 60 | 74.6 | 86.6 |
| 17 | $CH_3COO$ | $Cy_2$BIPHEMP | 1600 | Toluene | 10.0 | 60 | 60 | 92.6 | 82.2 |
| 18 | $C_6F_5O$ | $Cy_2$BIPHEMP | 1600 | Toluene | 10.0 | 60 | 60 | 80.2 | 80.0 |

TABLE 1-continued

Asymmetric hydrogenation of 2-pyridyl 2,8-bis(trifluoromethyl)-4-quinolyl ketone

| Example | X | Y (R) or (S) | S/C | LM | c % | P bar | T °C. | Conversion % | e.e. % |
|---|---|---|---|---|---|---|---|---|---|
| 19 | Cl | (3,4,5-TriMeO)MeOBIPHEP | 200 | Toluene | 1.4 | 60 | 60 | 98.7 | 84.6 |
| 20 | Br | Cy$_2$MeOBIPHEP | 6400 | Toluene | 10.0 | 60 | 60 | 97.9 | 92.4 |
| 21 | Cl | Cyp$_2$MeOBIPHEP | 200 | Toluene | 10.0 | 60 | 60 | 97.7 | 87.1 |
| 22 | Cl | Ipr$_2$MeOBIPHEP | 200 | Toluene | 10.0 | 60 | 60 | 97.7 | 87.5 |

EXAMPLE 23

The (R)- or (S)-P,P-dicyclohexyl-P',P'-diphenyl-(6,6'-dimethylbiphenyl- 2,2'-diyl)diphosphine used in the foregoing Examples was prepared as follows:

a) 32 ml of a tert.butyllithium solution (1.6M in pentane; 0.051 mol) were added to a solution, cooled to −76°, of 20.0 g (0.046 mol) of (R)-2,2'-diiodo-6,6'-dimethylbiphenyl (T. Frejd and T. Klingstedt, J. Chem. Soc., Chem. Commun. (1983) 1021) in 430 ml of absolute toluene and 90 ml of ether under Ar gasification and the mixture was stirred at −75° for ¾ hour. A solution of 20.1 g (0.092 mol) of chlorodiphenylphosphine in 100 ml of absolute toluene was subsequently added dropwise from a dropping funnel within ¼ hour, the mixture was stirred at −70° for 1 hour, and, after removing the cooling bath, at room temperature overnight. For the working-up, the reaction mixture, a grey-beige suspension, was treated with 150 ml of water, made alkaline with 80 ml of 3N NaOH and extracted with 300 ml of toluene. The organic phase was washed neutral with 2×200 ml of water, dried (Na$_2$SO$_4$), evaporated and the resulting residue (32.5 g; yellow oil) was chromatographed on 450 g of silica gel. In three main fractions there were eluted: with 4.5 l of hexane 3.2 g of unchanged starting material, with 15 l of hexane-toluene (95:5) mixture 13.1 g (71.3%) of enantiomeric pure monoiodide as white crystals and with 2 l of toluene 1.5 g of white crystalline (R)-BIPHEMP (GC content: 75%). For analysis, the monoiodide (13.1 g) was recrystallized from ethyl acetate/methanol: (R)-diphenyl-(2'-iodo-6,6'-dimethylbiphenyl-2-yl)phosphine; m.p.: 167.5°–168.4°; $[\alpha]_D^{20}$−44.8 (c=1; CHCl$_3$).

In an analogous manner there was prepared:

(S)-Diphenyl-(2'-iodo-6,6'-dimethylbiphenyl-2-yl)phosphine; m.p.: 167.5°–168.7°; $[\alpha]_D^{20}$+43.5 (c=1; CHCl$_3$).

b) 8.0 g (0.0162 mol) of (S)-diphenyl-(2'-iodo-6,6'-dimethylbiphenyl- 2-yl)phosphine were dissolved in a mixture of 100 ml of absolute toluene, 200 ml of ether and 0.5 ml of triethylamine under Ar gasification, cooled to −65°; 12 ml of tert.butyllithium solution (1.6M in pentane; 0.019 mol) were added and the reaction mixture was stirred at −60° for 1 hour. Subsequently, 5.0 g (0.021 mol) of dicyclohexylchlorophosphine were added in one portion, rinsed with a small amount of toluene and the grey-beige suspension was stirred at room temperature overnight. For the working-up, the mixture was treated with 50 ml of water and 50 ml of 3N NaOH, stirred for ¼ hour, extracted with 300 ml of toluene, the organic phase was washed once with 200 ml of water, dried (Na$_2$SO$_4$), filtered and evaporated. After recrystallization of the crude product [12 g; (S)-Cy$_2$BIPHEMP; GC content: 87%] from ethyl acetate there were obtained 6.2 g (68%) of (S)-P,P-dicyclohexyl-P',P'-diphenyl-(6,6'-dimethylbiphenyl- 2,2'-diyl)diphosphine as white crystals; m.p.: 185.4° (99.8% e.e. according to HPLC analysis on a Chircacel OD phase; GC content: 99.2%); $[\alpha]_D^{20}$+52.3 (c=1; CHCl$_3$)

In an analogous manner there was prepared:

(R)-P,P-Dicyclohexyl-P',P'-diphenyl-(6,6'-dimethylbiphenyl-2,2'-diyl)diphosphine; m.p.: 186°–186.9°; (99.8% e.e.; G: 99.3%): $[\alpha]_D^{20}$−52.8 (c=1; CHCl$_3$).

EXAMPLE 24

The following diphosphines used in Examples 9 and 12 were prepared in an analogous manner to Example 23:

(R)-Di-p-tolyl-(2'-iodo-6,6'-dimethylbiphenyl-2-yl)phosphine; m.p.: 135°–136°; $[\alpha]_D^{20}$−55.1 (c=1.0, CHCl$_3$);

(S)-di-p-tolyl-(2'-iodo-6,6'-dimethylbiphenyl-2-yl)phosphine; m.p.: 136.4°; $[\alpha]_D^{20}$+55.7 (c=1.0, CHCl$_3$);

(R)-P,P-dicyclohexyl-P',P'-di-p-tolyl-(6,6'-dimethylbiphenyl-2,2'diyl)diphosphine m.p.: 167° (98.6% e.e.; GC: 98%); $[\alpha]_D^{20}$−71.2 (c=1; CHCl$_3$);

(S)-P,P-dicyclohexyl-P',P'-di-p-tolyl-(6,6'-dimethylbiphenyl-2,2'-diyl)diphosphine; m.p.: 166.1°; (97% e.e.; GC: 98%); $[\alpha]_D^{20}$+69.4 (c=1; CHCl$_3$);

(R)-P,P-diphenyl-P',P'-di-2-thienyl-(6,6'-dimethylbiphenyl-2,2'-diyl)diphosphine; m.p.: 151°–151.3°; (99.2% e.e.; GC: 99.5%); $[\alpha]_D^{20}$+71.9 (c=1; CHCl$_3$);

(S)-P,P-diphenyl-P',P'-di-2-thienyl-(6,6'-dimethyl biphenyl-2,2'diyl)diphosphine; m.p.: 149°–150°; (99.9% e.e.; GC: 99.7%) $[\alpha]_D^{20}$−70.2 (c=1; CHCl$_3$).

EXAMPLE 25

The (R)-, respectively (S)-HOBIPHEP used according to Example 10 was prepared as follows:

A solution of 11,64 g (19,98 mmol) of (R)-(6,6'-dimethoxybiphenyl- 2,2'-diyl)bis(diphenylphosphine) [=(R)-MeOBIPHEP] in 200 ml CH$_2$Cl$_2$ (dried over a molekular sieve) was cooled under argon to −78°. A solution of 50 ml (50 mmol) 1M BBr$_3$ in CH$_2$Cl$_2$ was then slowly added whereby towards the end of the addition a white precipitate formed. The mixture was then warmed up to room temperature and stirred during 24 hours. After hydrolysis with 400 ml saturated NH$_4$Cl during one hour, separation of the phases, drying of the organic phase (CaCl$_2$) and evaporation there were obtained 12,5 g of a yellow powder. After chromatography on silica gel (90 g, hexane/CH$_2$Cl$_2$ 1:1, hexane/ethyl acetate 9:1→3:2) there were obtained 8,26 g (R)-HOBIPHEP as a white powder; mp 198,2°–199,4°; $[\alpha]_D^{20}$=−34,7° (c=0,9, CHCl$_3$).

By reaction of 0,65 g (1,1 mmol) (S)-MeOBIPHEP with 2,2 ml (2,2 mmol) 1M BBr$_3$ in CH$_2$Cl$_2$ in a manner analogous to the above there were obtained 0.35 g (S)-HOBIPHEP as a white powder; mp 199,5°– 200,5°; $[\alpha]_D^{20}$= +33,9° (c=1, CHCl$_3$).

EXAMPLE 26

The (R) or (S)-P,P-dicyclohexyl-P',P'-diphenyl-(6,6'-dimethoxybiphenyl-2,2'-diyl)diphosphine used according to Example 20 was prepared as follows:

a) In a mixture of 150 ml absolute toluene and 50 ml ether there were dissolved under argon 10,2 g (0,019 mol) (R)-diphenyl-(2'-iodo-6,6'-dimethoxybiphenyl-2-yl)phosphine. The solution was cooled to −70°, then 15 ml butyllithium solution (1,6M in hexane; 0,023 mol) were added and the reaction mixture was stirred for 45 minutes at −69°. Thereafter 10 g (0,043 mol) dicyclohexylchlorophosphine, dissolved in 50 ml toluene, where added dropwise at −65° during 15 minutes and the grey-beige suspension was then stirred during 1 hour at −65° and overnight at room temperature. For working-up, 85 ml water and 15 ml 3N NaOH were added to the mixture which was then stirred for 15 minutes and extracted with 300 ml toluene. The organic phase was washed 2 times with 150 ml water, dried ($Na_2SO_4$), filtrated and evaporated. After chromatographic filtration on 400 g silica gel (hexane-toluene 1:1) and recrystallization of the crude product from ethyl acetate there were obtained 4,7 g (R)-P,P-dicyclohexyl-P',P'-diphenyl-( 6,6'-dimethoxy-biphenyl-2,2'-diyl)diphosphine [(R)-$Cy_2$MeOBIPHEP] as white crystals; mp. 239,3°; $[\alpha]_D^{20}$=+ 10,3 (c=1; $CHCl_3$).

In a manner analogous to the above there was prepared:
(S)-P,P-dicyclohexyl-P',P'-diphenyl-(6,6'-dimethoxybiphenyl-2,2'-diyl) diphosphines [(S)-$Cy_2$MeOBIPHEP].

b) The (R)- and (S)-diphenyl-(2'-iodo-6,6'-dimethoxy-1,1'-biphenyl-2-yl)phosphine used as starting material were prepared as follows:

To a solution of 13,7 g (0,029 mol) (S)-2,2'-diiodo-6,6'-dimethoxy-1,1'-biphenyl dissolved in 200 ml absolute toluene and 50 ml ether there were added under argon and at −76° 18 ml of a tert.butyllithium solution (15% solution in pentane; 0,028 mol) and the mixture was stirred for 1 hour at −70°. From a dropping funnel there were subsequently added during 15 minutes a solution of 13 g (0,062 mol) chlorodiphenylphosphine in 50 ml absolute toluene. The mixture was then stirred for one hour at −70° and, after removing of the cooling bath, for 1 hour at room temperature. For working-up 70 ml of water were added to the reaction mixture which was then made alcaline with 30 ml 3N NaOH and then extracted with 500 ml of acetic acid ethyl ester. The organic phase was washed neutral with 150 ml water, dried ($Na_2SO_4$), evaporated and the resulting residue chromatographed on 300 g silica gel. In two main fractions there were eluted: with 2,1 l hexane-toluene (6:4) 4 g unaltered starting material and with 3,5 l hexane-toluene (1:1) 9,9 g enantiomerically pure monoiodide, as white crystals, which were used directly in the following reaction step. From the more polar fractions there could still be isolated about 120 mg crystalline (S)-MeOBIPHEP. For analysis purposes the sample of the monoiodide was recrystallized from ethyl acetate/ methanol:

(S)-diphenyl-(2'-iodo-6,6'-dimethoxy-1,1'-biphenyl-2-yl)phosphine; mp. 125,7°; $[\alpha]_D^{20}$=−9,0 (c=0,7; $CHCl_3$).

In an analogous manner there were prepared:
(R)-diphenyl-(2'-iodo-6,6'-dimethoxy-1,1'-biphenyl-2-yl)phosphine;
(R,S)-diphenyl-(2'-iodo-6,6'-dimethoxy-1,1'-biphenyl-2-yl)phospine; mp. 194,0°–194,4°.

c) The (R)- and (S)-2,2'-diiodo-6,6'-dimethoxy-1,1'-biphenyls used as starting material according to b) were prepared as follows:

12,15 g (0,05 mol) (S)-2,2'-diamino-6,6'-dimethoxy-1,1'-biphenyl were dissolved in a mixture of 288 ml water and 100 ml concentrated sulfuric acid ($H_2SO_4$) at ca. 30°–40° and the solution was cooled to 2° in a cooling bath. To this mixture there were added during 30 minutes at 2° a solution of 9,6 g (0,140 mol) sodium nitrite in 25 ml water and after completion of the addition this mixture was stirred for 30 minutes at 4°. Thereafter 150 ml of toluene were added. Then there was added from a dropping funnel during 5 minutes a solution of 42 g (0,253 mol) potassium iodide and 16,8 g (0,1 mol) iodide in 75 ml water and the mixture was stirred for 3 hours at room temperature. For working-up the reaction mixture was extracted with 300 ml ethyl acetate and 200 ml toluene, then the organic phase was washed 2× with 200 ml of a 10% aequous sodium thiosulfate solution and 2× with 150 ml water. The phases were then combined, dried ($Na_2SO_4$), evaporated and the resulting crude product chromatographed on 150 g silica gel. The elution was carried out with 10 l hexanedichloromethane (4:1 to 1:1) and then recrystallized from hexane. There were obtained 14,2 g white crystalline enantiomerically pure (S)-2,2'-diiodo-6,6'-dimethoxy-1,1'-biphenyl; mp. 163,5°; $[\alpha]_D^{20}$=− 55,1° (c=1; $CHCl_3$).

In an analogous manner there was prepared:
(R)-2,2'-diiodo-6,6'-dimethoxy 1,1'-biphenyl; mp 152°; $[\alpha]_D^{20}$=+54,4° (c=1; $CHCl_3$).

d) The (R)- and (S)- 2,2'-diamino-6,6'-dimethoxy-1,1'-biphenyls used as starting material according to c) were prepared as follows:

80 g (0,33 mol) racemic 2,2'-diamino-6,6'-dimethoxy-1,1'-biphenyl were dissolved in 600 ml ethyl acetate and 150 g (SS)-Di(phenylamino-carbonyl)-succininic acid[(SS)-DIPACOSA] were dissolved in a mixture of 400 ml ethyl acetate and 50 ml methanol at ca. 60°. The two solutions were combined at 60° and left for crystallization at room temperature overnight. After filtration, washing (150 ml ethyl acetate) and drying (14 mm Hg/room temperature; 30 minutes) of the white crystallizate there were obtained 173,9 g (S)- 2,2'-diamino-6,6'-dimethoxy-1,1'-biphenyl-(SS)-DIPACOSA (1:2)-adduct. [(S)/(R)-ratio: 99% to 1%]. For ameliorating the separation of the enantiomers the crystallizate (173,9 g) was suspended in 300 ml ethyl acetate and stirred for 15 minutes at 60°. The suspension was left overnight at room temperature then filtered and the filtrate washed with ethyl acetate (100 ml), dried (14 mm Hg/room temperature) and there were obtained 154 g (1:2)-adduct [(S)/(R)-ratio 99,7%/0,3%]. For the separation of the cleaving agent this material (154 g) was dissolved in 2 l ethyl acetate. Then there were added 700 ml water and the aquous phase was adjusted under stirring to pH 8 with a saturated sodium bicarbonate solution. After separation of the organic phase it was washed (200 ml water), dried ($Na_2SO_4$) and evaporated and there were obtained 30,9 g oily (S)-2,2'-diamino-6,6'-dimethoxy-1,1'biphenyl [(S)/(R)-ratio 99,8% /0,2%]. $[\alpha]_D^{20}$=−32° (c=1, $CHCl_3$).

In a manner analogous to the above, when starting from racemic diamine, the cleaving with (RR)-DIPACOSA yielded oily (R)-2,2'-diamino-6,6'-dimethoxy1,1'-biphenyl which was recrystallized from diethyl ether. [(S)/(R)-ratio 0%/100%]; mp. 86,9°, $[\alpha]_D^{20}$=+32,8° (c=1, $CHCl_3$).

In a manner analogous to the above the following diphosphines, used in Examples 21 and 22, were prepared:

(S)-P,P-dicyclopentyl-P',P'-diphenyl-(6,6'-dimethoxybiphenyl-2,2'-diyl)diphosphine; [(S)-$Cyp_2$MeOBIPHEP]; mp. 210,9°; $[\alpha]_D^{20}$=−15,7° (c=0, 4, $CHCl_3$);

(R)-P,P-dicyclopentyl-P',P'-diphenyl-(6,6'-dimethoxybiphenyl-2,2'-diyl)diphosphine; [(R)-$Cyp_2$MeOBIPHEP];

(S)-P,P-diisopropyl-P',P'-diphenyl-(6,6'-dimethoxybiphenyl-2,2'-diyl)diphosphine; [(S)-$Ipr_2$ MeOBIPHEP]; mp. 147,9°; $[\alpha]_D^{20}$=−29° (c=0,5, $CHCl_3$);

(R)-P,P-diisopropyl-P',P'-diphenyl-(6,6'-dimethoxybiphenyl-2,2'-diyl)diphosphine; [(R)-Ipr₂ MeOBIPHEP].

EXAMPLE 27

18 g of platinum oxide and 18 g of active charcoal were prehydrogenated in 500 ml of methanol for 1 hour under normal conditions in a 5 l hydrogenation flask. Subsequently, a solution of 185.0 g (0.50 mol) of (S)-α-(2-pyridyl)-2,8-bis(trifluoromethyl)-4-quinolinemethanol (>99% e.e.) and 60 ml of 37% hydrochloric acid in 1300 ml of methanol were added. The hydrogenation was carried out at 40° under normal pressure for 8 hours, whereby 37 l of hydrogen were taken up. The conversion was 100% according to TLC. After cooling the catalyst was filtered off, washed with methanol and the filtrate was evaporated. The yellow, crystalline residue (210 g of hydrochloride) consisted of 85% of the erythro isomer and 15% of the corresponding threo isomer according to GC. The e.e. values of both diastereomers were at least 98% (GC of a silylated sample).

50 g of the crude hydrochloride were converted by partition between 150 ml of 1N sodium hydroxide solution and 0.5 l of ether into the corresponding mixture of the erythro base and threo base (43 g) which was chromatographed on 1 kg of silica gel in order to separate the isomers. Using a (20:1) mixture of methylene chloride and methanol saturated with 25% ammonium hydroxide as the eluting agent there were obtained, in addition to mixed fractions, 4.2 g of a threo isomer and 19 g of pure erythro isomer.

Both isomers were recrystallized from methanol-toluene for analysis.

(S)-α-[(S)-2-Piperidinyl]-2,8-bis(trifluoromethyl)-4-quinolinemethanol (threo); white crystals; m.p. 175°–176°; $[\alpha]_D^{20}$ –21.8 (c=0.4, methanol);

(S)-α-[(R)-2-piperidinyl]-2,8-bis(trifluoromethyl)-4-quinolinemethanol (erythro); white crystals; m.p. 170.5°–171.0°; $[\alpha]_D^{20}$=–33.8 (c=0.4, methanol).

In an analogous manner there were prepared:

(R)-α-[(R)-2-Piperidinyl]-2,8-bis(trifluoromethyl)-4-quinolinemethanol (threo); m.p. 176°–177°; $[\alpha]_D^{20}$+22.0 (c=0.4, methanol);

(R)-α-[(S)-2-piperidinyl]-2,8-bis(trifluoromethyl)-4-quinolinemethanol (erythro); m.p. 170.5°–171.0°; $[\alpha]_D^{20}$+35.5 (c=0.4, Methanol).

We claim:

1. A process for the manufacture of compounds of the formula:

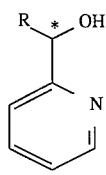

I wherein

R represents aryl or heteroaryl, by asymmetrically hydrogenating a ketone of the formula:

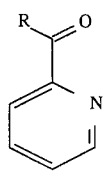

II wherein

R is as above, in the presence of a rhodium-diphosphine complex of the formula:

III wherein

X, Y and L are the following:
X=halogenide, Z—COO⁻, phenolate or halogenated phenolate;
Z=lower alkyl, phenyl, halogenated lower alkyl or halogenated phenyl;
Y=a chiral, atropisomeric diphosphine ligand of the formula:

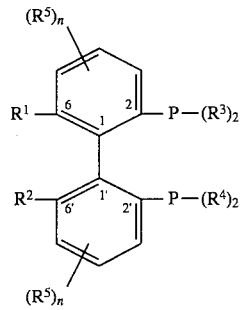

IV or of the formula:

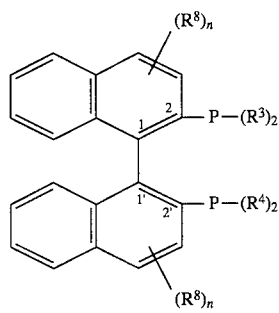

V or a ferrocenyl-diphosphine of the formula:

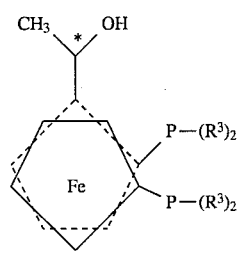

VI wherein:
R¹ and R² independently=lower alkyl, lower alkoxy, di-lower alkylamino, hydroxy, protected hydroxy, hydroxymethyl, protected hydroxymethyl, or R¹ and R² together are

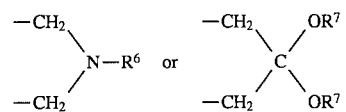

m=integer 3, 4, or 5;
R⁶=lower alkyl, phenyl, or benzyl;
R⁷=lower alkyl or both R⁷'s together di- or trimethylene;

$R^3$ and $R^4$ independently=lower alkyl, phenyl, cycloalkyl, a five-membered heteroaromatic group or a group of the formula:

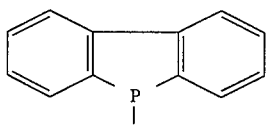

$R^5$=lower alkyl or lower alkoxy,
$R^8$=methyl, ethyl, halogen —OH, —NH$_2$, acetylamino, —NO$_2$, or —SO$_3$H, preferably in the 5,5'-position,
n=integer 0, 1, 2, or 3, and
L=neutral ligand.

2. The process of claim 1, wherein R is pyridyl or quinolyl.

3. The process of claim 2 wherein R is 4-pyridyl or 4-quinolyl.

4. The process of claim 3 wherein R is a group of the formula:

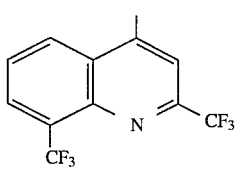

5. The process according to claim 4 wherein the asymmetric hydrogenation is carried out using a catalyst of formula:

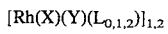  III in which Y is a chiral, atropisomeric ligand of formula:

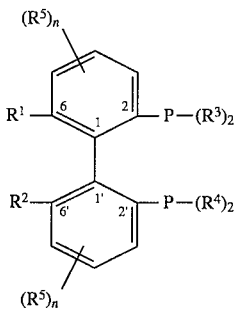  IV and $R^1$, $R^2$, $R^3$, $R^4$, and $R^5$ are as above.

6. The process of claim 5 wherein X is a halogenide.

7. The process of claim 6 wherein X is chloride or bromide, $R^1$ and $R^2$ are the same and are methyl or methoxy, $R^3$ and $R^4$ are different and are phenyl and cyclohexyl, and n=0.

8. The process of claim 7 wherein X is chloride and $R^1$ and $R^2$ are both methyl.

9. The process of claim 7 wherein X is bromide and $R^1$ and $R^2$ are both methyl.

10. The process of claim 7 wherein X is bromide and $R^1$ and $R^2$ are both methoxy.

11. The process of claim 6 wherein X is chloride.

12. The process of claim 11 wherein $R^1$ and $R^2$ are both methoxy.

13. The process of claim 12 wherein n=0.

14. The process of claim 13 wherein $R^3$ and $R^4$ are both phenyl.

15. The process of claim 13 wherein $R^3$ and $R^4$ are both 3,4,5-trimethoxyphenyl.

16. The process of claim 13 wherein $R^3$ is cyclopentyl and $R^4$ is phenyl.

17. The process of claim 13 wherein $R^3$ is isopropyl and $R^4$ is phenyl.

18. The process of claim 11 wherein $R^1$ and $R^2$ are both methyl.

19. The process of claim 18 wherein n=0.

20. The process of claim 19 wherein $R^3$ and $R^4$ are both cyclohexyl.

21. The process of claim 19 wherein $R^3$ is phenyl and $R^4$ is thienyl.

22. The process of claim 19 wherein $R^3$ is cyclohexyl and $R^4$ is p-tolyl.

23. The process of claim 6 wherein n=0, X is chloride and $R^1$ and $R^2$ are both hydroxyl.

24. The process of claim 23 wherein n=0.

25. The process of claim 24 wherein $R^3$ and $R^4$ are both phenyl.

26. The process of claim 6 wherein X is bromide.

27. The process of claim 26 wherein $R^1$ and $R^2$ are both methyl.

28. The process of claim 27 wherein n=0.

29. The process of claim 28 wherein $R^3$ is cyclohexyl and $R^4$ is p-tolyl.

30. The process of claim 5 wherein X is halogenated phenolate.

31. The process of claim 30 wherein X is $C_6F_5O$.

32. The process of claim 31 wherein n=0.

33. The process of claim 32 wherein $R^1$ and $R^2$ are both methyl, and $R^3$ is cyclohexyl and $R^4$ is phenyl.

34. The process of claim 5 wherein X is Z—COO$^-$.

35. The process of claim 34 wherein Z is lower alkyl.

36. The process of claim 35 wherein Z is methyl.

37. The process of claim 36 wherein n=0.

38. The process of claim 37 wherein $R^1$ and $R^2$ are both methyl, and $R^3$ is cyclohexyl and $R^4$ is phenyl.

39. The process according to claim 4 wherein the asymmetric hydrogenation is carried out using a catalyst of formula:

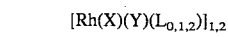  III in which Y is a chiral, ferrocenyl-diphosphine of the formula:

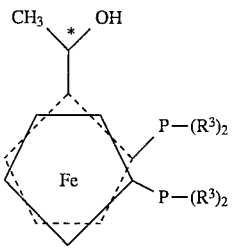  VI

40. The process of claim 39 wherein X is halogenide.

41. The process of claim 40 wherein $R^3$ is phenyl.

42. The process of claim 41 wherein X is chloride.

43. The process of claim 41 wherein X is bromide.

44. The process of claim 41 wherein X is iodide.

* * * * *